United States Patent [19]

Nickl et al.

[11] 4,062,973
[45] Dec. 13, 1977

[54] SULFUR-CONTAINING DERIVATIVES OF CYCLOHEXYLPHENYL-ETHANE

[75] Inventors: Josef Nickl; Berthold Narr; Erich Müller; Josef Roch; Walter Haarmann, all of Biberach, Germany

[73] Assignee: Boehringer Ingelheim GmbH, Ingelheim am Rhein, Germany

[21] Appl. No.: 730,122

[22] Filed: Oct. 6, 1976

[30] Foreign Application Priority Data

Oct. 16, 1975 Germany .................... 2546319

[51] Int. Cl.[2] .............. C07C 149/40; C07C 147/107; A61K 31/215; A61K 31/19
[52] U.S. Cl. .................. 424/308; 260/293.73; 260/516; 260/515 A; 260/515 M; 260/558 S; 424/248.5; 424/267; 424/317; 424/324; 544/158; 560/11; 560/15
[58] Field of Search .......... 260/470, 516, 515 A, 260/515 M; 424/308, 317

[56] References Cited

U.S. PATENT DOCUMENTS

| | | |
|---|---|---|
| 3,549,691 | 12/1970 | Leigh et al. .................... 260/470 |
| 3,993,683 | 11/1976 | Nickl et al. .................... 260/470 |
| 4,000,183 | 12/1976 | Haas et al. .................... 560/255 |

FOREIGN PATENT DOCUMENTS 2,443,401   3/1975   Germany ...................... 260/470

Primary Examiner—James O. Thomas
Assistant Examiner—Michael Shippen
Attorney, Agent, or Firm—Hammond & Littell

[57] ABSTRACT

Compounds of the formula

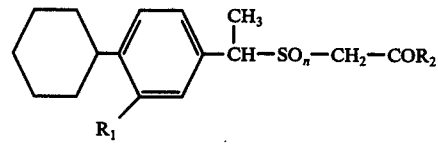

wherein
  $R_1$ is hydrogen or halogen,
  $R_2$ is hydroxyl, alkoxy of 1 to 6 carbon atoms, aralkoxy of 7 to 10 carbon atoms, amino, (alkyl of 1 to 3 carbon atoms)-amino, piperidino or morpholino, and
  $n$ is 0, 1 or 2, diastereoisomers thereof and, when $R_2$ is hydroxyl, non-toxic, pharmacologically acceptable salts thereof formed with an inorganic or organic base; the compounds, their diastereoisomers and the salts are useful as antithrombotics, anti-hypercholesteremics and anti-hyperglyceridemics.

8 Claims, No Drawings

SULFUR-CONTAINING DERIVATIVES OF CYCLOHEXYLPHENYL-ETHANE

This invention relates to novel sulfur-containing derivatives of cyclohexylphenyl-ethane, as well as to various methods of preparing these compounds.

More particularly, the present invention relates to a novel class of sulfur-containing derivatives of cyclohexylphenyl-ethane represented by the formula

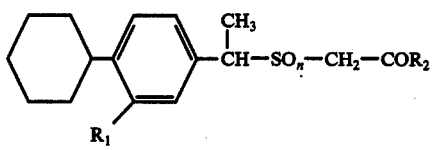

wherein $R^1$ is hydrogen or halogen, $R_2$ is hydroxyl, alkoxy of 1 to 6 carbon atoms, aralkoxy of 7 to 10 carbon atoms, amino, (alkyl of 1 to 3 carbon atoms)-amino, piperidino or morpholino, and $n$ is 0, 1 or 2, diastereoisomers thereof and, when $R_2$ is hydroxyl, non-toxic, pharmacologically acceptable salts thereof formed with an inorganic or organic base.

Particularly preferred embodiments of substituents $R_1$ and $R_2$ in formula I are the following:

$R_1$ — hydrogen or chlorine; and $R_2$ — hydroxyl, methoxy, ethoxy, propoxy, isopropoxy, butoxy, isoamyloxy, hexyloxy, benzyloxy, amino, isopropylamino, piperidino or morpholino.

The compounds embraced by formula I may be prepared by the following methods:

METHOD A

For the preparation of a compound of the formula I wherein $n$ is 0, by reacting a cyclohexylphenyl-ethane derivative of the formula

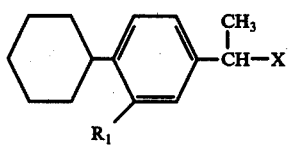

wherein $R_1$ has the same meanings as in formula I, and X is hydroxyl or halogen, with w thioglycolic acid derivative of the formula

wherein $R_2$ has the same meanings as in formula I.

The reaction is advantageously carried out in a solvent, such as dimethyl sulfoxide, and optionally in the presence of a base, such as potassium carbonate, triethylamine or pyridine, or, when X is hydroxyl, in the presence of an acid, such as hydrochloric acid or sulfuric acid, at temperatures between 0° and 100° C, preferably, however, between 5° and 30° C.

When $R_2$ in formula III is alkoxy or aralkoxy, this substituent may be converted into hydroxyl during the reaction.

METHOD B

For the preparation of a compound of the formula I wherein $n$ is 1 or 2, by oxidizing a compound of the formula

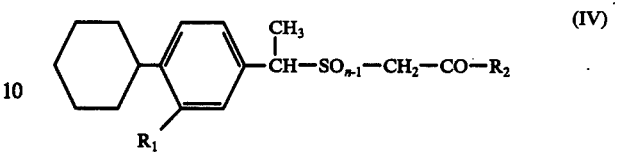

wherein $R_1$, $R_2$ and $n$ have the same meanings as in formula I.

The oxidation is preferably carried out in the presence of a solvent, such as in water, a mixture of water and pyridine, acetone, glacial acetic acid, dilute sulfuric acid or trifluoroacetic acid, and advantageously at temperatures between −80° and 100° C, depending upon the particular oxidizing agent which is used.

For the preparation of a compound of the formula I wherein $n$ is 1, the oxidation is advantageously carried out with an equimolar amount of the oxidizing agent; for example, with hydrogen peroxide in glacial acetic acid at 0° to 20° C or in acetone at 0° to 60° C; or with a peracid, such as performic acid, in glacial acetic acid or trifluoroacetic acid at 0° to 50° C; or with sodium metaperiodate in aqueous methanol or ethanol at 15° to 25° C; with tert.butyl hypochlorite in methanol at −80° to −30° C; or with iodobenzene dichloride in aqueous pyridine at 0° to 5° C; or with nitric acid in glacial acetic acid at 0° to 20° C; or with chromic acid in glacial acetic acid or acetone at 0° to 20° C.

For the preparation of a compound of the formula I wherein $n$ is 2, the oxidation is carried out with one or two equivalents of the oxidizing agent; for example, with hydrogen peroxide in glacial acetic acid at 20° to 100° C or in acetone at 0° to 60° C; or with a peracid, such as performic acid or m-chloro-perbenzoic acid in glacial acetic acid, trifluoroacetic acid or chloroform, at temperatures between 0° and 50° C; or with nitric acid in glacial acetic acid at 0° to 20° C; or with chromic acid or potassium permanganate in glacial acetic acid, water/sulfuric acid or acetone at 0° to 20° C. Thus, if $n$ is 1 in a compound of the formula IV, the reaction is preferably carried out with 2 equivalents of the particular oxidizing agent and correspondingly with one equivalent of the oxidizing agent if $n$ is 2.

METHOD C

For the preparation of a compound of the formula I wherein $R_2$ is other than hydroxyl, by reacting a carboxylic acid of the formula

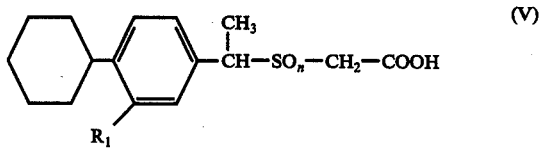

wherein $R_1$ and $n$ have the same meanings as in formula I, or a halide or anhydride thereof, with a compound of the formula

wherein $R_2'$ is alkyl of 1 to 6 carbon atoms, aralkyl of 7 to 10 carbon atoms, amino, (alkyl of 1 to 3 carbon atoms)-amino, piperidino or morpholino, and Y is hydroxyl, chlorine, bromine, iodine, a sulfonic acid radical, a phosphoric acid radical or, when $R_2'$ is amino or (alkyl of 1 to 3 carbon atoms)-amino, piperidino or morpholino, also hydrogen.

The reaction is advantageously carried out in the presence of a solvent, such as ether, chloroform, benzene, tetrahydrofuran, dioxane, dimethylformamide, dimethyl sulfoxide, hexamethyl-phosphoric acid triamide or an excess of the compound of the formula VI, optionally in the presence of an acid-activating and/or dehydrating agent and optionally in the presence of a base, at temperatures between $-20°$ and $150°$ C.

In those instances where the compound of the formula VI is a carbinol, such as methanol, ethanol, propanol, isopropanol, butanol, isoamylalcohol, hexanol or benzyl alcohol, the reaction is advantageously carried out in the presence of an acid, such as sulfuric acid, p-toluene-sulfonic acid or hydrochloric acid, an acid-activating agent, such as phosphorus oxychloride, thionyl chloride or chlorosulfonic acid, a dehydrating agent, such as cyclohexyl carbodiimide, carbonyl diimidazole or 2,2-dimethoxypropane, or with a corresponding chloroformic acid ester, optionally in the presence of a base, such as potassium carbonate or triethylamine, preferably at temperatures between $20°$ and $100°$ C.

If the compound of the formula VI is a sulfate such as dimethylsulfate, a corresponding phosphate such as triethylphosphate, or a corresponding halide such as methyl iodide, ethyl iodide or propyl iodide, the reaction is advantageously carried out in a dipolar aprotic solvent, in the presence of a base such as potassium carbonate, calcium hydroxide or sodium hydroxide, preferably at temperatures between $20°$ and $80°$ C. The reaction may, however, also be carried out as a phase transfer-catalyzed two-phase reaction, for example between chloroform and water, in the presence of a quaternary ammonium salt such as tetrabutylammonium iodide.

If the compound of the formula VI is an amine such as ammonia, isopropylamine, piperidine or morpholine, the reaction is advantageously carried out in the presence of a dehydrating agent, such as cyclohexyl carbodiimide or carbonyl diimidazole, and preferably in the presence of a solvent, such as dioxane or tetrahydrofuran, at temperatures between $10°$ and $50°$ C.

In those instances where method A, B or C yields a compound of the formula I wherein $R_2$ is other than hydroxyl, that compound may, if desired, subsequently be converted into the corresponding free carboxylic acid by means of hydrolysis. Furthermore, a compound of the formula I wherein $R_2$ is hydroxyl may, if desired, subsequently be converted into a non-toxic, pharmacologically acceptable salt thereof with an inorganic or organic base, such as with sodium hydroxide, potassium hydroxide or cyclohexylamine.

The starting compounds of the formulas II to VI may be obtained by methods described in the literature, as illustrated in the examples below.

The following examples illustrate the present invention and will enable others skilled in the art to understand it more completely. It should be understood, however, that the invention is not limited solely to the particular examples given below.

In these examples the following chromatographic materials were used:

For column chromatography: silicagel manufactured by the Woelm Company, grain size 0.05 to 0.2 mm.

For thin-layer chromatography (TLC):

Carrier A = silicagel polygram plates SIL G/UV 254 manufactured by Macherey, Nagel & Co.

Carrier B = prepared silicagel plates F 254 manufactured by Merck.

EXAMPLE A 1-(4'-Cyclohexyl-phenyl)-1-hydroxy-ethane 11.4 gm (0.3 mol) of sodium borohydride were added in small portions at $20°-25°$ C to 60.7 gm (0.3 mol) of 4'-cyclohexyl-acetophenone (m.p. $66°-67°$ C) in 300 ml of methanol while stirring vigorously and cooling on ice. The resulting mixture was then stirred for another hour at room temperature, and the reaction product was precipitated with acidified ice water. After suction filtering, washing and drying, 62.6 gm of crystalline material were obtained. A sample, recrystallized from petroleum ether, melted at $81.5°-82.5°$ C.

Elemental analysis: $C_{14}H_{20}O$; (204.31); Calculated: C - 82.30%; H - 9.87%; Found: C - 82.40%; H - 9.92%.

EXAMPLE B 1-(4'-Cyclohexylphenyl)-1-chloro-ethane 61.3 gm of crude 1-(4'-cyclohexyl-phenyl)-1-hydroxyethane were dissolved in 600 ml of benzene, and 100 gm of dry magnesium sulfate were added. Anhydrous hydrogen chloride gas was then introduced at room temperature, while stirring, until TLC of a sample (carrier A, cyclohexane/ethyl acetate = 4/1) showed completion of the reaction. The magnesium sulfate was suction-filtered off, and the organic phase was washed with water, dried and evaporated. 68.4 gm of an oil were obtained with an $R_f$-value of 0.8 (carrier A, cyclohexane/ethyl acetate = 4/1).

The following compounds were prepared in analogous manner:

1-(3'-Chloro-4'-cyclohexyl-phenyl)-1-hydroxy-ethane, an oil, $R_f$-value 0.3 on carrier A with cyclohexane/ethyl acetate=4/1.

1-(3'-Chloro-4'-cyclohexyl-phenyl)-1-chloro-ethane, an oil, $R_f$-value 0.8 on carrier A with cyclohexane/ethyl acetate =4/1.

EXAMPLE 1

Methyl [1-(4'-cyclohexyl-phenyl)-ethylthio]-acetate 50.6 gm (0.45 mol) of 1-(4'-cyclohexyl-phenyl)-1-chloro-ethane and 48 gm (0.45 mol) of methyl thioglycolate were dissolved in 300 ml of dimethyl sulfoxide, and 69 gm (0.5 mol) of dry potassium carbonate were added in small portions at room temperature, while stirring. The resulting mixture was stirred for 2 hours, 600 ml of water were then added, and the reaction product was extracted with toluene. After washing, drying and evaporating 79 gm of an oil were obtained. $R_f$-value: 0.7 (carrier A with cyclohexane/ethyl acetate = 4/1).

Elemental analysis: $C_{17}H_{24}O_2S$ (292.44); Calculated: C-69.82%; H-8.27%; S-10.96%; Found: C-69.58%; H-8.39%; S-10.86%.

EXAMPLE 2

Methyl [1-(3'-chloro-4'-cyclohexyl-phenyl)-ethylthio]-acetate was prepared analogous to Example 1 from 1-(3'-chloro-4'-cyclohexyl-penyl)-1-chloro-ethane and methyl thioglycolate. Oil; $R_f$-value: 0.8 (carrier A with cyclohexane/ethyl acetate = 4/1); yield: 95% of theory.

Elemental analysis: $C_{17}H_{23}ClO_2S$ (330.89); Calculated: C-62.92%; H-7.01%; Cl-1.72%; S-9.69%; Found: C-63.10%; H-7.20%; Cl-10.60%; S-9.85%.

EXAMPLE 3

[1-(4'-Cyclohexyl-phenyl)-ethylthio]-acetic acid 87.5 gm (0.3 mol) of methyl [1-(4'-cyclohexyl-phenyl)-ethylthio]-acetate were boiled for 1 hour with a solution of 25 gm of potassium hydroxide in 300 ml of isopropanol. Upon standing, the potassium salt of the acid crystallized out, which was isolated by suction filtration and washed with isopropanol and ether. Yield: 83.3 (87.8% of theory); m.p. 232°-233° C.

Elemental analysis: $C_{16}H_{21}KO_2S$ (316.50); Calculated: C - 60.70%; H - 6.69%; S - 10.13%; Found: C - 60.40%; H - 6.88%; S - 10.10%.

By acidification the free acid was obtained as an oil. $R_f$value: 0.6 (carrier A with cyclohexane/ethyl acetate = 2/1).

Elemental analysis: $C_{16}H_{22}O_2S$ (278.42); Calculated: C - 69.03%; H - 7.97%; S - 11.52%; Found: C - 69.00%; H - 7.95%; S - 11.27%.

EXAMPLE 4

[1-(3'-Chloro-4'-cyclohexyl-phenyl)-ethylthio]-acetic acid was prepared analogous to Example 3 from methyl [1-(3'-chloro-4'-cyclohexyl-phenyl)-ethylthio]-acetate by hydrolysis. Yield: 84% of theory; m.p. 80°-82° C (from petroleum ether).

EXAMPLE 5

[1-(4'-Cyclohexyl-phenyl)-ethylthio]-acetic acid 491 gm (2.4 mol) of 1-(4'-cyclohexy-phenyl)-1-hydroxy-ethane were dissolved in 2.4 liters of toluene and 250 ml (332 gm) of 80% thioglycolic acid were added. While cooling on ice water and stirring vigorously, 220 ml (369 gm = 2.4 mols) of phosphorus oxychloride were added dropwise to the mixture at a rate such that the internal temperature remained at about 40° C. Afterwards, the reaction mixture was stirred at room temperature for 2 hours more. 2 liters of ice water were then stirred in, and the organic phase was separated, dried and evaporated. 675 gm of crude acid were obtained. The acid was dissolved in a solution of 148 gm of potassium hydroxide in 1.48 liters of ethanol. Upon cooling, the potassium salt crystallized out. Working up of the mother liquor yielded 623 gm (82% of theory) of the potassium salt, m.p. 232°-233° C. Upon acidification 550 gm (82% of theory) of the free acid were obtained as an oil.

EXAMPLE 6

[1-(3'-chloro-4'-cyclohexyl-phenyl)-ethylthio]-acetic acid amide 13.8 gm (0.085 mol) of carbonyl diimidazole were added to 17.7 gm (0.057 mol) of [1-(3'-chloro-4'-cyclohexylphenyl)-ethylthio]-acetic acid in 200 ml of dry tetrahydrofuran. After the evolution of carbon dioxide had ceased (about 20 minutes), dry ammonia gas was introduced into the solution of the imidazolide. After standing overnight, the mixture was evaporated in vacuo, and the residue was distributed between ethyl acetate and dilute hydrochloric acid. After washing and drying 17.5 gm of an oil with an $R_f$-value of 0.3 were obtained from the ethyl acetate phase (carrier A with cyclohexane/ethyl acetate = 1/1). The oil was crystallized from cyclohexane. Yield: 13.4 gm (75.8% of theory); m.p. 92°-94° C.

Elemental anaylsis: $C_{16}H_{22}ClNOS$ (311.89); Calculated: Cl - 11.37%; S - 10.28%; Found: Cl - 11.45%; S - 10.45%.

EXAMPLE 7

[1-(3'-Chloro-4'-cyclohexyl-phenyl)-ethylthio]-acetic acid piperidide was prepared analogous to Example 6 from [1-(3'-chloro-4'-cyclohexyl-phenyl)-ethylthio]-acetic acid, carbonyl diimidazole and piperidine. Yield: 99% of theory; an oil, $R_f$-value: 0.7 (carrier A with cyclohexane/ethyl acetate = 1/1).

Elemental analysis: $C_{21}H_{30}ClNOS$ (380.00); Calculated: C-66.38%; H-7.96%; Cl-9.33%; N-3.69%; S-8.44%; Found: C-66.20%; H-7.54%; Cl-9.18%; N-3.85%; S-8.18%.

EXAMPLE 8

[1-(3'-Chloro-4'-cyclohexyl-phenyl)-ethylthio]-acetic acid morpholide was prepared analogous to Example 6 from [1-(3'-chloro-4'-cyclohexyl-phenyl)-ethylthio]-acetic acid, carbonyl diimidazole and morpholine. Yield; 95% of theory; an oil, $R_f$-value: 0.5 (carrier A with cyclohexane/ethyl acetate= 1/1).

Elemental analysis: $C_{20}H_{28}ClNO_2S$ (381.975); Calculated: C-62.89%; H-7.39%; Cl-9.28%; N-3.67%; S-8.39%; Found: C-63.02%; H-7.48%; Cl-9.14%; N-3.92%; S-8.60%.

EXAMPLE 9

Diastereoisomeric [1-(4'-cyclohexyl-phenyl)-ethylsulfinyl]-acetic acids a. Slightly soluble isomer 61.5 gm (0.22 mol) of [1-(4'-cyclohexyl-phenyl)-ethylthio]-acetic acid were dissolved in 200 ml of glacial acetic acid, and 21.4 gm (0.23 mol) of 36.8% hydrogen peroxide were added dropwise at 15° C. Afterwards, the mixture was allowed to stand at room temperature for 1 ½ hours, whereupon the reaction product was suction-filtered off and washed with petroleum ether. Yield: 31.3 gm (48.6% of theory). m.p. 152°-154° C (decomp.).

Elemental analysis: $C_{16}H_{22}O_3S$ (294.40) Calculated: C - 65.28%; H - 7.53%; S - 10.89%; Found: C - 65.50%; H - 7.64%; S - 10.87%.

Characteristic signals in the NMR-spectrum ($CDCl_3$ - $CD_3OD$):

$CH_2$: singlet at 3.5 ppm

CH: quartet at 4.25 ppm (J = 7 Hz)

b. Readily soluble isomer

The acetic acid filtrate of the slightly soluble isomer was evaporated in vacuo, and the residue (33.1 gm) was recrystallized twice from toluene. Yield: 18.1 gm (28.2% of theory); m.p. 128°-132° C (decomp.).

Elemental analysis: $C_{16}H_{22}O_3S$ (294.40) Calculated: C - 65.28%; H - 7.53%; S - 10.89%; Found: C - 65.40%; H - 7.49%; S - 10.82%.

Characteristic signals in the NMR-spectrum ($CDCl_3$ - $CD_3OD$):

CH$_2$: duplet at 3.4 ppm (J = 8 Hz)
CH: quartet at 4.2 ppm (J = 7 Hz)

EXAMPLE 10

Methyl [1-(4'-cyclohexyl-phenyl)-ethylsulfinyl]-acetate 2.94 gm (10 millimols) of [1-(4'-cyclohexyl-phenyl-ethylsulfinyl]-acetic acid (slightly soluble isomer, m.p. 152°-154° C) were dissolved in a mixture of 30 ml of benzene and 0.5 gm of methanol, and subsequently 2.48 gm (12 millimols) of dicyclohexyl carbodiimide were added. The resulting mixture was stirred for 1 hour, 10 ml of 2 N acetic acid were then added, and the dicylohexylurea was suction-filtered off. 2.4 gm (78% of theory) of the desired product were obtained from the organic phase after evaporation and recrystallization from cyclohexane-petroleum ether. M.p. 112°-114° C.

Elemental analysis- C$_{17}$H$_{24}$O$_3$S (308.45); Calculated: C - 66.20%; H - 7.84%; S - 10.40%; Found: C - 66.40%; H - 7.94%; S - 10.37%.

Characteristic signals in the NMR-spectrum (CDCl$_3$):
CH$_2$: double duplet at 3.4 ppm (J = 14 Hz)
CH: quartet at 4.05 ppm (J = 7 Hz, δν= 22 Hz).

EXAMPLE 11

Methyl [1-(4'-cyclohexyl-phenyl)-ethylsulfinyl]-acetate 200 gm (0.681 mol) of [1-(4'-cyclohexyl-phenyl)-ethylsulfinyl]-acetic acid (slightly soluble isomer, m.p. 152°-154° C) were dissolved in 680 ml of dimethyl sulfoxide, and 96.6 gm (0.75 mol) ethyl-diisopropyl-amine were added while cooling. Then 106 gm (0.75 mol = 46.6 ml) of methyl iodide were added dropwise at 20° C over a period of 20 minutes. The resulting mixture was stirred for another hour, and the reaction product was precipitated with 2 liters of water. After suction-filtering and drying, the product was recrystallized from petroleum ether and then isopropanol. Yield: 169.5 gm = 80.7% of theory; m.p. 113°-115° C (from petroleum ether).

EXAMPLE 12

Methyl [1-(4'-cyclohexyl-phenyl)-ethylsulfinyl]-acetate was prepared analogously to Example 10 from [1-(4'-cyclohexyl-phenyl)-ethylsulfinyl]-acetic acid (readily soluble isomer, m.p. 128°-132° C). Yield: 71% of theory, m.p. 81°-85° C.

EXAMPLE 13

Ethyl [1-(4'-cyclohexyl-phenyl)-ethylsulfinyl]-acetate was prepared analogously to Example 11 from [1-(4'-cyclohexyl-phenyl)-ethylsulfinyl]-acetic acid (m.p. 152-154° C) with ethyl iodide. Yield: 68% of theory; m.p. 75-77° C (from petroleum ether).

Elemental analysis: C$_{18}$H$_{26}$O$_3$S (322.47) Calculated: C - 67.03%; H - 8.14%; S - 9.94%; Found: C - 67.30%; H - 8.16%; S - 10.04%.

NMR-spectrum (CDCl$_3$):
CH$_2$: double duplet at 3.36 ppm (J = 14 Hz, δν= 29 Hz)

EXAMPLE 14

Isopropyl [1-(4'-cyclohexyl-phenyl)-ethylsulfinyl]-acetate

A solution of 10.0 gm (34 millimols) of [1-(4'-cyclohexyl-phenyl)-ethylsulfinyl]-acetic acid (m.p. 152°-154° C) in 50 ml of dry tetrahydrofuran was admixed with 6.1 gm (37.4 millimols) of carbonyl diimidazole and, after evolution of carbon dioxide had ceased (about 20 minutes), with 2.2 gm (37 millimols) of isopropanol. The mixture was allowed to react overnight and was then evaporated in vacuo, and the residue was distributed between water and ethyl acetate. After washing with an aqueous sodium carbonate solution and dilute hydrochloric acid and drying, the organic phase was evaporated, and the residue was chromatographed on silicagel with cyclohexane/ethyl acetate (¼). The eluate was evaporated, and the residue was recrystallized from petroleum ether.

Yield: 5.3 gm (46% of theory); m.p. 95°-97° C.

Elemental analysis: C$_{19}$H$_{28}$O$_3$S (336.60); Calculated: C - 67.82%; H - 8.39%; Found: C - 67.90%; H - 8.39%.

EXAMPLE 15

Isobutyl [1-(4'-cyclohexyl-phenyl)-ethylsulfinyl]-acetate was prepared analogous to Example 14 from [1-(4'-cyclohexylphenyl)-ethylsulfinyl]-acetic acid (m.p. 152°-154° C) and isobutanol by means of carbonyl diimidazole. Yield: 68% of theory; m.p. 79°-81° C (from petroleum ether).

Elemental analysis: C$_{20}$H$_{30}$O$_3$S (350.53); Calculated: C - 68.52%; H - 8.63%; S - 9.15%; Found: C - 68.50%; H - 8.58%; S - 9.06%;

EXAMPLE 16

Isoamyl [1-(4'-cyclohexyl-phenyl)-ethylsulfinyl]-acetate was prepared analogous to Example 14 from [1-(4'-cyclohexyl-phenyl)-ethylsulfinyl]-acetic acid (m.p. 152°-154° C) and isoamyl alcohol by means of carbonyl diimidazole. Yield: 75.0% of theory; m.p. 69°-70° C (from petroleum ether).

Elemental analysis: C$_{21}$H$_{32}$O$_3$S (364.55); Calculated: C - 69.19%; H - 8.85%; S - 8.80%; Found: C - 69.40%; H - 8.78%; S - 8.78%.

EXAMPLE 17 n-Hexyl [1-(4'-cyclohexyl-phenyl)-ethylsulfinyl]-acetate was prepared analogous to Example 14 from [1-(4'-cyclohexyl-phenyl)-ethylsulfinyl]-acetic acid (m.p. 152°-154° C) and n-hexanol by means of carbonyl diimidazole. Yield: 82% of theory; m.p. 73°-74° C (from petroleum ether).

Elemental analysis: C$_{22}$H$_{34}$O$_3$S (378.58); Calculated: C - 69.80%; H - 9.05%; S - 8.47%; Found: C - 69.70%; H - 9.38%; S - 8.24%.

EXAMPLE 18

Benzyl [1-(4'-cyclohexyl-phenyl)-ethylsulfinyl]-acetate was prepared analogous to Example 14 from [1-(4'-cyclohexyl-phenyl)-ethylsulfinyl]-acetic acid (m.p. 152°-154° C) and benzyl alcohol by means of carbonyl diimidazole. Yield: 78% of theory; m.p. 76°-77° C (from cyclohexane/petroleum ether = ½).

Elemental analysis: C$_{23}$H$_{28}$O$_3$S (384.54); Calculated: C - 71.84%; H - 7.34%; S - 8.34%; Found: C - 71.80%; H - 7.58%; S - 8.22%.

EXAMPLE 19

[1-(4'-Cyclohexyl-phenyl)-ethylsulfinyl]-acetic acid amide 10.0 gm (34 millimols) of [1-(4'-cyclohexyl-phenyl)-ethylsulfinyl]-acetic acid (m.p. 152°-154° C) were dissolved in 50 ml of absolute tetrahydrofuran, and 6.1 gm (37 millimols) of carbonyl diimidazole were added. After the evolution of carbon dioxide had ceased (about 20 minutes), dry ammonia gas was introduced until the mixture was saturated. After standing overnight, the mixture was evaporated, and the residue was distributed between water and ethyl acetate. The organic phase was washed with an aqueous sodium carbonate solution and with dilute hydrochloric acid, dried and evaporated, and the residue was recrystallized from isopropanol.

Yield: 7.5 gm (75.4% of theory); m.p. 199°–201° C.

Elemental analysis: $C_{16}H_{23}NO_2S$ (293.44); Calculated: C-65.49%; H-7.90%; N-4.77%; S-10.93%; Found: C-65.60%; H-7.95%; N-4.99%; S-10.86%.

EXAMPLE 20

[1-(4'-Cyclohexyl-phenyl)-ethylsulfinyl]-acetic acid isopropylamide was prepared analogous to Example 19 from [1-(4'-cyclohexyl-phenyl)-ethylsulfinyl]-acetic acid (m.p. 152°–154°0 C) and isopropylamine by means of carbonyl diimidazole. Purification by column chromatography on silicagel with ethyl acetate. Yield: 82% of theory; m.p. 124°–126° C (from cyclohexane).

Elemental analysis: $C_{19}H_{29}NO_2S$ (335.52) Calculated: C-68.02%; H-8.71%; N-4.18%; S-9.56%; Found: C-68.00%; H-8.98%; N-4.20%; S-9.38%.

EXAMPLE 21

[1-(4'-Cyclohexyl-phenyl)-ethylsulfinyl]-acetic acid morpholide was prepared analogous to Example 19 from [1-(4'-cyclohexyl-phenyl)-ethylsulfinyl]-acetic acid (m.p. 152°–154° C) and morpholine by means of carbonyl diimidazole. Further purification was carried out by column chromatography on silicagel with benzene/ethyl acetate/methanol = 8/4/1.

Yield: 87% of theory; m.p. 112°–114° C (from cyclohexane).

Elemental analysis: $C_{20}H_{29}NO_3S$ (363.53); CaLculated: C - 66.08%; H - 8.04%; S - 8.82%; Found: C - 66.20%; H - 8.07%; S - 8.68%.

EXAMPLE 22

[1-(4'-Cyclohexyl-phenyl)-ethylsulfinyl]-acetic acid piperidide was prepared analogous to Example 19 from [1-(4'-cyclohexyl-phenyl)-ethylsulfinyl]-acetic acid (m.p. - 152°–154° C) and piperidine by means of carbonyl diimidazole. Purification by column chromatography on silicagel with ethyl acetate. Yield: 67% of theory; m.p. 94°–96° C (from cyclohexane).

Elemental analysis: $C_{21}H_{31}NO_2S$ (361.55); Calculated: C - 69.76%; H - 8.64%; S - 8.87%; Found: C - 69.60%; H - 8.60%; S - 8.89%.

EXAMPLE 23

Diastereoisomeric [1-(3'-chloro-4'-cyclohexyl-phenyl)-ethylsulfinyl]-acetic acids were prepared analogous to Example 9 by oxidation of [1-(3'-chloro-4'-cyclohexyl-phenyl)-ethylthio]-acetic acid in glacial acetic acid with hydrogen peroxide.

a. Slightly soluble isomer

Yield: 47% of theory; m.p. 160°–162° C (decomp.; from glacial acetic acid)

Elemental analysis: $C_{16}H_{21}ClO_3S$ (328.87) Calculated: C-58.44%; H-6.44%; Cl-10.78%; S-9.75%; Found: C-58.30%; H-6.26%; Cl-10.88%; S-9.76%.

Characteristic signals in the NMR-spectrum ($CDCl_3$ - $CD_3OD$): $CH_2$: singlet at 3.55 ppm b. Readily soluble isomer Yield: 30% of theory; m.p. 141°–143° C (decomp.; from benzene/ cyclohexane = 2/1).

Elemental analysis: $C_{16}H_{21}ClO_3S$ (328.87); Calculated: C-58.44%; H-6.44%; Cl-10.78%; S-9.75%; Found: C-58.50%; H-6.23%; Cl-10.92%; S-9.78%.

NMR-spectrum ($CDCl_3$ - $CD_3OD$):

$CH_2$: double duplet at 3.65 ppm (J = 7 ppm).

EXAMPLE 24

Methyl [1-(3'-chloro-4'-cyclohexyl-phenyl)-ethylsulfinyl]-acetate was prepared analogous to Example 11 from [1-(3'-chloro-4'-cyclohexyl-phenyl)-ethylsulfinyl]-acetic acid (slightly soluble isomer, m.p. 160°–162° C) and methyl iodide in the presence of potassium carbonate. Yield: 66% of theory; m.p. 93°–95° C (from cyclohexane/petroleum ether=2/1).

Elemental analysis: $C_{17}H_{23}ClO_3S$ (342.90); Calculated: C-59.55%; H-6.76%; Cl-10.34%; S-9.35%; Found: C-59.80%; H-6.86%; Cl-10.34%; S-9.34%.

NMR-spectrum ($CDCl_3$):

$CH_2$: double duplet at 3.45 ppm.

EXAMPLE 25

Methyl [1-(3'-chloro-4'-cyclohexyl-phenyl)-ethylsulfinyl]-acetate was prepared analogous to Example 11 from [1-(3'-chloro-4'-cyclohexyl-phenyl)-ethylsulfinyl]-acetic acid (readily soluble isomer, m.p. 141°–143° C) and methyl iodide in the presence of potassium carbonate. Purification by column chromatography on silicagel with cyclohexane/ethyl acetate = 1/1. Yield: 34% of theory; an oil, $R_f$-value: 0.35 on carrier B with cyclohexane/ethyl acetate = 1/1.

Elemental analysis: $C_{17}H_{23}ClO_3S$ (342.90);

Calculated: C-59.55%; H-6.76%; Cl-10.34%; S-9.35%; Found: C-59.90%; H-6.96%; Cl-10.13%; S-9.10%.

NMR-spectrum ($CDCl_3$):

$CH_2$: singlet at 3.32 ppm.

EXAMPLE 26

Ethyl [1-(3'-chloro-4'-cyclohexyl-phenyl)-ethylsulfinyl]-acetate was prepared analogous to Example 11 from [1-(3'-chloro-4'-cyclohexyl-phenyl)-ethylsulfinyl]-acetic acid (m. p. 160°–162° C) and ethyl iodide in the presence of potassium carbonate. Yield: 53.6% of theory; m.p. 80-82° C (from cyclohexane/petroleum ether = ½).

Elemental analysis: $C_{18}H_{25}ClO_3S$ (356.92); Calculated: C-60.57%; H-7.06%; Cl-9.93%; S-8.98%; Found: C-60.50%; H-7.00%; Cl-9.98%; S-9.10%.

NMR-spectrum ($CDCl_3$):

$CH_2$: double duplet at 3.45 ppm (J = 14 Hz)

EXAMPLE 27

Ethyl [1-(3'-chloro-4'-cyclohexylphenyl)-ethylsulfinyl]-acetate was prepared analogous to Example 11 from [1-(3'-chloro-4'-cyclohexyl-phenyl)-ethylsulfinyl]-acetic acid (m. p. 141°–143° C) and ethyl iodide in the presence of potassium carbonate. Purification by column chromatography on silicagel with cyclohexane/ethyl acetate = 1/1. Yield: 27% of theory; m.p. 102°–104° C (cyclohexane/petroleum ether = ½).

Elemental analysis: $C_{18}H_{25}ClO_3S$ (356.92); Calculated: C-60.57%; H-7.06%; Cl-9.93%; S-8.98%; Found: C-60.80%; H-7.04%; Cl-10.07%; S-9.02%.

EXAMPLE 28

Diastereoisomeric [1-(3'-chloro-4'-cyclohexyl-phenyl)-ethylsulfinyl]-acetic acid amides a. Isomer slightly soluble in methanol 13.4 gm (42,1 millimols) of [1-(3'-chloro-4'-cyclohexyl-phenyl)-ethylthio]-acetic acid amide were oxidized in 75 ml of glacial acetic acid with 4.2 gm of 36.3% hydrogen peroxide at room temperature (duration: 1 hour). The reaction product was precipitated with water, dried and dissolved in 60 ml of methanol. From this methanolic solution 6.7 gm (48.5% of theory) of the desired product crystallized out, which was collected by filtration; m.p. 187°–189° C (decomp.).

Elemental anlysis: $C_{16}H_{22}ClNO_2S$ (327.89) Calculated: C-58.61%; H-6.76%; Cl-10.81%; N-4.27%; S-9.78%; Found: C-59.30%; H-6.85%; Cl-10.63%; N-4.27%; S-9.62%.

NMR-spectrum (CDCl$_3$ -CD$_3$OD):
CH$_2$: double duplet at 3.4 ppm (J = 14 Hz)

b. Isomer readily soluble in methanol

The methanolic filtrate was evaporated, and the residue was recrystallized from much ethyl acetate and subsequently from toluene. Yield: 3.5 gm (25.4% of theory); m.p. 145°–147° C.

Elemental analysis: $C_{16}H_{23}ClNO_2S$ (327.89); Calculated: C-58.61%; H-6.76%; Cl-10.81%; N-4.27%; S-9.78%; Found: C-58.90%; H-6.77%; Cl-10.60%; N-4.23%; S-10.02%.

EXAMPLE 29

[1-(3'-Chloro-4'-cyclohexyl-phenyl)-ethylsulfinyl]-acetic acid piperidide was prepared analogous to Example 28 from [1-(3'-chloro-4'-cyclohexyl-phenyl)-ethylthio]-acetic acid piperidide by oxidation with hydrogen peroxide in glacial acetic acid. Purification was carried out by column chromatography on silicagel with toluene/ethyl acetate/methanol = 8/4/1; yield: 90% of theory.

The mixture of the two diastereoisomers thus obtained was an oil with R$_f$-values of 0.6 and 0.5 (carrier A with toluene/ethyl acetate/methanol = 8/4).

Elemental analysis: $C_{21}H_{30}ClNO_2S$ (395.99); Calculated: C-63.70%; H-7.64%; Cl-8.95%; N-3.54%; S-8.10%; Found: C-64.50%; H-7.79%; Cl-8.11%; N-3.40%; S-8.34%.

EXAMPLE 30

[1-(3'-Chloro-4'-cyclohexyl-phenyl)-ethylsulfinyl]-acetic acid morpholide was prepared analogous to Example 28 from [1-(3'-chloro-4'-cyclohexyl-phenyl)-ethylthio]-acetic acid morpholide by oxidation with hydrogen peroxide in glacial acetic acid. Purification was carried out by column chromatography on silicagel with toluene/ethyl acetate/methanol = 8/4/1. Yield: 83% of theory. The mixture of the two diastereoisomers thus obtained was an oil with R$_f$-values of 0.4 and 0.3 (carrier B with toluene/ethyl acetate/methanol = 8/4/1).

Elemental analysis: $C_{20}H_{28}ClNO_3S$ (397.96) Calculated: C-60.36%; H-7.09%; Cl-8.91%; N-3.52%; S-8.06%; Found: C-60.70%; H-7.19%; Cl-8.68%; N-3.31%; S-7.90%.

EXAMPLE 31

[1 -(4'-Cyclohexyl-phenyl)-ethylsulfonyl]acetic acid 5.0 gm (17 millimols) of [1-(4'-cyclohexyl-phenyl)-ethylsulfinyl]-acetic acid (m.p. 152°–154° C) were suspended in a mixture of 50 ml of glacial acetic acid and 10 ml of water, and 2.7 gm (17 millimols) of potassium permanganate were added in small portions at 20° to 25° C, while stirring vigorously. Afterwards, the mixture was stirred for another hour, admixed with 150 ml of water, the manganese dioxide was reduced with sodium sulfite, and the reaction product was extracted with ethyl acetate. After washing with water, drying and evaporating the extract solution, the residue was crystallized from cyclohexane. Yield: 4.1 gm (77% of theory); m.p. 104°–105° C.

Elemental analysis: Calculated: C - 61.91%; H - 7.14%; S - 10.33%; Found: C - 61.90%; H - 7.14%; S - 10.38%.

Characteristic IR-bands (CH$_2$Cl$_2$) at 1130 and 1310 cm$^{-1}$ (SO$_2$).

EXAMPLE 32

Methyl [1-(4'-cyclohexyl-phenyl)-ethylsulfonyl]-acetate was prepared analogous to Example 31 from metyl [1(4'-cyclohexyl-phenyl)-ethylsulfinyl]-acetate (m.p. 112°–114° C) by oxidation with potassium permanganate. Yield: 83% of theory; m.p. 81°–83° C (from cyclohexane).

Elemental analysis: $C_{17}H_{24}O_4S$ (324.45); Calculated: C - 62.93%; H - 7.46%; S - 9.88%; Found: C - 62.80%; H - 7.40%; S - 9.96%.

Characteristic IR-bands (CH$_2$Cl$_2$) at 1130 and 1310 cm$^{-1}$ (SO$_2$) and at 1740 cm$^{-1}$ (ester).

EXAMPLE 33

[1-(4'-Cyclohexyl-phenyl)-ethylsulfonyl]-acetic acid amide was prepared analogous to Example 31 from [1-(4'-cyclohexylphenyl)-ethylsulfinyl]-acetic acid amide by oxidation with potassium permanganate. Yield: 75% of theory; m.p. 150–152° C (from benzene).

Elemental analysis: $C_{16}H_{23}NO_3S$ (309.44); Calculated: C-62.11%; H-7.49%; N-4.53%; S-10.36%; Found: C-62.10%; H-7.45%; N-4.41%; S-10.20%.

EXAMPLE 34

[1-(4'-Cyclohexyl-phenyl)-ethylsulfonyl]-acetic acid piperidide was prepared analogous to Example 31 from [1-(4'-cyclohexyl-phenyl)-ethylsulfinyl]-acetic acid piperidide by oxidation with potassium permanganate. Yield: 62% of theory; m.p. 92–94° C (from cyclohexane/petroleum ether = 1/1).

Elemental analysis: $C_{21}H_{31}NO_3S$ (3.77.55); Calculated: C-66.81%; H-8.28%; N-3.71%; S-8.49%; Found: C-66.90%; H-8.15%; N-3.84%; S-8.49%.

EXAMPLE 35

[1-(4'-Cyclohexyl-phenyl)-ethylsulfonyl]-acetic acid was prepared analogous to Example 31 from [1-(4'-cyclohexyl-phenyl)-ethylthio]-acetic acid by oxidation with double the amount of potassium permanganate. Yield: 82% of theory; m.p. 104°–105° C (from cyclohexane).

EXAMPLE 36

Methyl [1-(4'-cyclohexyl-phenyl)-ethylsulfonyl]-acetate was prepared analogous to Example 11 from [1-(4'- cyclohexylphenyl)-ethylsulfonyl]-acetic acid by esterification with methyl iodide in the presence of N-ethyl-diisopropylamine. Yield: 86% of theory; m.p. 82°-84° C.

EXAMPLE 37

[1-(4'-Cyclohexyl-phenyl)-ethylsulfonyl]-acetic acid amide was prepared analogous to Example 19 from [1-(4'-cyclohexylphenyl)-ethylsulfonyl]-acetic acid and ammonia by means of carbonyl diimidazole. Yield: 78% of theory; m.p. 149°-151° C.

The compounds of the present invention have useful pharmacodynamic properties. More particularly, the compounds exhibit antithrombotic, anti-hypercholesteremic and antihyperglyceridemic activities in warm-blooded animals, such as mice, and are therefore useful for prophylactic treatment of arterial thromboembolisms and diseases caused by arterial occlusion.

The antithrombotic activity and the toxicity of the compounds of this invention were ascertained by the standard test methods described below, and the tables show the results obtained therefrom for a few representative species, where A = [1-(4'-cyclohexyl-phenyl)-ethylsulfinyl]-acetic acid (m.p. 152°-154° C);
B = methyl [1-(4'-cyclohexyl-phenyl)-ethylsulfinyl]-acetate (m.p. 113°-115° C);
C = methyl [1-(3'-chloro-4'-cyclohexyl-phenyl)-ethylsulfinyl]-acetate (m.p. 93°-95° C);
D = methyl [1-(3'-chloro-4'-cyclohexyl-phenyl)-ethylsulfinyl]-acetate (m.p. 80°-82° C); and
E = [1-(3'-chloro-4'-cyclohexyl-phenyl)-ethylsulfinyl]-acetic acid piperidide (an oil with $R_f$-values of 0.6 and 0.5).

1. Determination of platelet aggregation by the method of Born and Cross (see J. Physiol. 170, 397 (1964)):

The platelet aggregation was measured in the platelet-rich plasma of healthy human donors. The alterations of the optical density of the platelet suspension was measured and recorded photometrically after the addition of commercial collagen manufactured by Hormonchemie, Munich, Germany, containing 1 mgm of collagen fibrils per ml. From the angle of inclination of the density curve, the rate of aggregation was estimated (Vmax). The optical density (O.D.) was taken at the point on the curve where the most light was transmitted. Small doses of collagen were chosen, but sufficient to give irreversible aggregation. To provoke maximum aggregation, about 0.01 ml of the collagen solution was added to 1 ml of platelet-rich plasma.

The numbers in Table I represent the % reduction in the aggregation rate (Vmax) and the % change in optical density (O.D.), compared with a control batch without addition of a test compound.

TABLE I

| | % Reduction after addition of $10^{-4}$ mol/lit. | |
|---|---|---|
| Compound | Vmax | O.D. |
| C | 85 | 89 |
| D | 87 | 89 |
| E | 90 | 92 |

2. Determination of the prolongation of the bleeding time:

To determine the effect on the bleeding time, 10 mgm/kg of the test compound were administered orally to awake, unanesthetized mice. After 1 hour, and again after 3 hours, about 0.5 mm from the end of the tail of each animal was cut off, and the exuded blood was carefully soaked up into filter paper every 30 seconds. The number of drops of blood so obtained provided a measure for the bleeding time (5 animals/experiment).

The numbers in Table II represent the prolongation in %, compared with an untreated control group:

TABLE II

| | Prolongation of the bleeding time in % after | |
|---|---|---|
| Compound | 1 hour | 3 hours |
| A | 300 | 122 |
| B | 117 | 51 |
| D | 49 | |
| E | 37 | |

3. Acute Toxicity:

The acute toxicity of the compounds was determined in white mice (observation time: 14 days) after oral application of a single dose:

TABLE III

| Compound | Acute toxicity |
|---|---|
| A | > 1000 mgm/kg (0 out of 10 animals died) |
| B | > 1000 mgm/kg (0 out of 10 animals died) |
| E | > 1000 mgm/kg (0 out of 10 animals died) |

For pharmaceutical purposes the compounds according to the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.16 to 0.83 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 38

Tablets

The tablet composition is compounded from the following ingredients:

| | |
|---|---|
| [1-(4'-Cyclohexyl-phenyl)-ethyl-sulfinyl]-acetic acid | 30.0 parts |
| Lactose | 38.0 parts |
| Potato starch | 26.0 parts |
| Polyvinylpyrrolidone | 5.0 parts |
| Magnesium stearate | 1.0 parts |
| Total | 100.0 parts |

Preparation:

The active ingredient is admixed with the lactose and the potato starch, the mixture is homogeneously moistened with an ethanolic 20% solution of the polyvinylpyrrolidone, granulated through a 1.5 mm-mesh screen, dried at 45° C and again passed through a 1.0 mm-mesh screen. The granulate thus obtained is admixed with the magnesium stearate, and the composition is compressed into 100 mgm-tablets. Each tablet is an oral dosage unit composition and contains 30 mgm of the active ingredient.

EXAMPLE 39

Coated pills

The pill core composition is compounded from the following ingredients:

| [1-(4'-Cyclohexyl-phenyl)-ethyl-sulfinyl]-acetic acid | | 15.0 parts |
|---|---|---|
| Lactose | | 14.0 parts |
| Corn starch | | 8.0 parts |
| Polyvinylpyrrolidone | | 2.5 parts |
| Magnesium stearate | | 0.5 parts |
| | Total | 40.0 parts |

Preparation:

The active ingredient is admixed with the lactose and the corn starch, the mixture is homogeneously moistened with an ethanolic 20% solution of the polyvinylpyrrolidone, granulated through a 1.5 mm-mesh screen, dried at 45° C and again passed through a 1.0 mm-mesh screen. The granulate thus obtained is admixed with the magnesium stearate, and the composition is compressed into 40 mgm-pill cores, which are then coated with a thin shell consisting essentially of a mixture of sugar and talcum. The coated pills are finally polished with beeswax. Each coated pill is an oral dosage unit composition containing 15 mgm of the active ingredient.

EXAMPLE 40

Hypodermic solution

The solution is compounded from the following ingredients:

| [1-(4'-Cyclohexyl-phenyl)-ethyl-sulfinyl]-acetic acid | 10.0 parts |
|---|---|
| Polyethyleneglycol 600 | 100.0 parts |
| Distilled water    q.s.ad | 2000.0 parts by vol. |

Preparation:

The polyethyleneglycol and the active ingredient are dissolved in a sufficient amount of distilled water in an atmosphere of nitrogen; the distilled water had been pretreated by boiling and cooling in an atmosphere of nitrogen. The resulting solution is then diluted with analogously pretreated distilled water to the indicated volume and filtered until free from suspended particles. All of these steps must be performed in diffused light. The filtrate is subsequently filled into brown 2 cc-ampules in an atmosphere of nitrogen, which are finally sterilized for 20 minutes at 120° C and sealed. The contents of each ampule are an injectable solution containing 10 mgm of the active ingredient.

EXAMPLE 41

Drop solution

The solution is compounded from the following ingredients:

| [1-(4'-Cyclohexyl-phenyl)-ethyl-sulfinyl]-acetic acid | 10.0 parts |
|---|---|
| Cane sugar | 350.0 parts |
| Sorbic acid | 1.0 parts |
| Flavoring | 50.0 parts |
| Ethanol | 200.0 parts by vol. |
| Polyethyleneglycol | 100.0 parts by vol. |
| Distilled water    q.s.ad | 1000.0 parts by vol. |

Preparation:

The sorbic acid is dissolved in the ethanol, an equal volume of distilled water is added, and the active ingredient is dissolved therein (solution 1). The sugar is dissolved in the remaining distilled water (solution 2). Solution 2, the polyethyleneglycol 600 and the flavoring are added, while stirring, to solution 1, and the mixture is filtered through a suitable filter. 1 ml of the solution contains 10 mgm of the active ingredient and is an effective oral dosage unit composition.

EXAMPLE 42

Rectal suppositories

The suppository composition is compounded from the following ingredients:

| [1-(4'-Cyclohexyl-phenyl)-ethyl-sulfinyl]-acetic acid | | 50.0 parts |
|---|---|---|
| Suppository base (e.g. cocoa butter) | | 1500.0 parts |
| | Total | 1550.0 parts |

Preparation:

The finely pulverized active ingredient is stirred with the aid of an immersion homogenizer into the suppository base which had previously been melted and cooled to 40° C. 1550 mgm-portions of the composition are poured at 38° C into cooled suppository molds and allowed to harden therein. Each suppository is a rectal dosage unit composition containing 50 mgm of the active ingredient.

Any one of the other compounds of the present invention may be substituted for the particular active ingredient in Examples 38 through 41. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

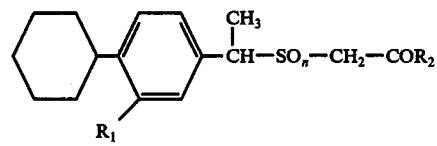

wherein $R_1$ is hydrogen or halogen, $R_2$ is hydroxyl, alkoxy of 1 to 6 carbon atoms or aralkoxy of 7 to 10 carbon atoms, and $n$ is 0, 1 or 2, a diastereoisomer thereof or, when $R_2$ is hydroxyl, a non-toxic, pharmacologically acceptable salt thereof formed with an inorganic or organic base.

2. A compound of claim 1, wherein $R_1$ is hydrogen or chlorine, $R_2$ is hydroxyl, methoxy, ethoxy, propoxy, isopropoxy, butoxy, isoamyloxy, hexyloxy or benzyloxy, and $n$ is 0, 1 or 2.

3. A compound of claim 1, which is [1-(4'-cyclohexyl-phenyl)-ethylsulfinyl]-acetic acid having a melting point of 152°–154° C, or a salt thereof.

4. The compound of claim 1, which is ethyl [1-(4'-cyclohexyl-phenyl)-ethylsulfinyl]-acetate having a melting point of 113°–115° C.

5. The compound of claim 1, which is methyl [1-(3'-chloro-4'-cyclohexyl-phenyl)-ethylsulfinyl]-acetate having a melting point of 93°–95° C.

6. The compound of claim 1, which is ethyl [1-(3'-chloro-4'-cyclohexyl-phenyl)-ethylsulfinyl]-acetate having a melting point of 80°–82° C.

7. An antithrombotic pharmaceutical dosage unit composition consisting essentially of an inert pharmaceutical carrier and an effective antithrombotic amount of a compound of claim 1.

8. The method of preventing or relieving thrombosis in a warm-blooded animal, which comprises perorally, parenterally or rectally administering to said animal an effective antithrombotic amount of a compound of claim 1.

* * * * *